(12) United States Patent
Allen (10) Patent No.: US 8,661,614 B2
(45) Date of Patent: Mar. 4, 2014

(54) GROMMET DEVICE WITH FLEXIBLE BOWED MEMBERS AND METHODS OF USING THEREOF

(75) Inventor: Kraig Herman Allen, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 13/587,460

(22) Filed: Aug. 16, 2012

(65) Prior Publication Data
US 2013/0046289 A1 Feb. 21, 2013

Related U.S. Application Data

(60) Provisional application No. 61/524,547, filed on Aug. 17, 2011.

(51) Int. Cl.
*F16L 5/00* (2006.01)

(52) U.S. Cl.
USPC .................................................. 16/2.1; 16/2.2

(58) Field of Classification Search
USPC ............................................. 16/2.1, 2.2, 2.3
See application file for complete search history.

(56) References Cited

U.S. PATENT DOCUMENTS

| | | | |
|---|---|---|---|
| 2,438,499 A | 3/1948 | Hartman | |
| 2,664,458 A | 12/1953 | Rapata | |
| 3,110,337 A | 11/1963 | Biesecker | |
| 3,217,584 A | 11/1965 | Amesbury | |
| 3,245,428 A * | 4/1966 | Klimak et al. | 137/493 |
| 3,309,955 A | 3/1967 | Turnbull et al. | |
| 3,611,861 A | 10/1971 | Schulze | |
| 3,651,734 A | 3/1972 | McSherry | |
| 3,678,797 A | 7/1972 | Seckerson | |
| 3,964,364 A | 6/1976 | Pie | |
| 4,136,599 A | 1/1979 | Hammer, Jr. | |
| 4,276,806 A | 7/1981 | Morel | |
| 4,843,675 A | 7/1989 | Diamantis | |
| 5,645,282 A | 7/1997 | Belter | |
| 5,775,859 A | 7/1998 | Anscher | |
| 5,975,820 A | 11/1999 | Kirchen | |
| 6,051,795 A | 4/2000 | Fisher et al. | |
| 6,088,876 A | 7/2000 | Daoud | |
| 6,099,812 A | 8/2000 | Allen et al. | |
| 6,278,061 B1 * | 8/2001 | Daoud | 174/659 |
| 6,364,586 B1 | 4/2002 | Okada | |
| 6,382,575 B1 | 5/2002 | Frush et al. | |
| 6,505,386 B1 | 1/2003 | Allie | |
| 6,514,023 B2 | 2/2003 | Moerke | |
| 6,854,946 B2 | 2/2005 | Bauer | |
| 7,677,850 B2 * | 3/2010 | Sano | 411/45 |
| 2006/0261695 A1 | 11/2006 | Terrill et al. | |
| 2010/0261955 A1 | 10/2010 | O'Hern et al. | |
| 2011/0014005 A1 | 1/2011 | Shinozaki | |
| 2011/0046491 A1 | 2/2011 | Diamond | |
| 2011/0091301 A1 | 4/2011 | Shimizu et al. | |
| 2011/0170982 A1 | 7/2011 | Watanabe | |
| 2011/0197405 A1 | 8/2011 | Kato et al. | |

FOREIGN PATENT DOCUMENTS

JP 2005270192 A 10/2005

* cited by examiner

*Primary Examiner* — Roberta Delisle
(74) *Attorney, Agent, or Firm* — Hayes Soloway P.C.

(57) ABSTRACT

A grommet device and method of using a grommet device is provided. The grommet device includes a base structure and a top structure connected to the base structure with a plurality of sidewalls, wherein an aperture having a central axis is formed interior of the plurality of sidewalk. At least one flexible bowed element having a first end, a second end and a middle portion is connected to the base structure at the first end and the top structure at the second end, wherein the middle portion is positioned within the aperture.

20 Claims, 6 Drawing Sheets

```
┌─────────────────────────────────────────────────────────┐
│ A grommet device having a base structure and a top      │
│ structure is provided, wherein the top structure is     │
│ connected to the base structure with a plurality of     │─── 102
│ sidewalls, and wherein an aperture having a central     │
│ axis is formed interior of the plurality of sidewalls   │
└─────────────────────────────────────────────────────────┘
                              │
┌─────────────────────────────────────────────────────────┐
│ A shaft of at least one medical instrument is inserted  │
│ into the aperture, wherein at least one flexible bowed  │
│ element having a first end, a second end and a middle   │
│ portion contacts the shaft of the at least one medical  │─── 104
│ instrument at the middle portion, wherein the first end │
│ of the at least one flexible bowed element is connected │
│ to the base structure, and the second end of the at     │
│ least one flexible bowed element is connected to the    │
│ top structure                                           │
└─────────────────────────────────────────────────────────┘
                              │
┌─────────────────────────────────────────────────────────┐
│ The shaft of the at least one medical instrument is     │
│ retained within the aperture with the middle portion    │─── 106
│ of the at least one flexible bowed element              │
└─────────────────────────────────────────────────────────┘
```

FIG. 6

GROMMET DEVICE WITH FLEXIBLE BOWED MEMBERS AND METHODS OF USING THEREOF

CROSS REFERENCE TO RELATED APPLICATION

This application claims benefit of U.S. Provisional Application Ser. No. 61/524,547, entitled, "Grommet Device with Flexible Bowed Members and Method of Using Thereof" filed Aug. 17, 2011, the entire disclosure of which is incorporated herein by reference.

FIELD OF THE DISCLOSURE

The present disclosure is generally related to grommets and more particularly is related to a grommet device with flexible bowed members and method of using thereof.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Conventionally, medical instruments are often held in containers or trays with holes and grommets. The grommets may be positioned within the hole and provide a secure interface between the medical instrument and the hole within the container or tray. Often, the grommets are sized to match a certain shaft size of a medical instrument, and a container or tray may include a variety of different sized grommets, each specifically engineered and designed to hold one of a variety of medical instruments. These medical instruments have varying shaft sizes and it often becomes tedious to search for the appropriately sized grommet that matches a particular shaft size of the medical instrument. It is not uncommon for a medical tray to have fifty or more grommets, with a dozen or more different sizes. Thus, the time it takes to match a specific medical instrument to a specifically sized grommet may result in inefficient use of valuable time.

Thus, a heretofore unaddressed need exists in the industry to address the aforementioned deficiencies and inadequacies.

SUMMARY OF THE DISCLOSURE

Embodiments of the present disclosure provide a grommet device. Briefly described, in architecture, one embodiment of the system, among others, can be implemented as follows. The grommet device includes a base structure and a top structure connected to the base structure with a plurality of sidewalls, wherein an aperture having a central axis is formed interior of the plurality of sidewalls. At least one flexible bowed element having a first end, a second end and a middle portion is connected to the base structure at the first end and the top structure at the second end, wherein the middle portion is positioned within the aperture.

The present disclosure can also be viewed as providing methods of securing a medical instrument within a sterilization tray. In this regard, one embodiment of such a method, among others, can be broadly summarized by the following steps: providing a grommet device having a base structure and a top structure, wherein the top structure is connected to the base structure with a plurality of sidewalls, and wherein an aperture having a central axis is formed interior of the plurality of sidewalls; inserting a shaft of at least one medical instrument into the aperture, wherein at least one flexible bowed element having a first end, a second end and a middle portion contacts the shaft of the at least one medical instrument at the middle portion, wherein the first end of the at least one flexible bowed element is connected to the base structure, and the second end of the at least one flexible bowed element is connected to the top structure; and retaining the shaft of the at least one medical instrument within the aperture with the middle portion of the at least one flexible bowed element.

The present disclosure can also be viewed as providing a medical instrument sterilization system. Briefly described, in architecture, one embodiment of the system, among others, can be implemented as follows. The medical instrument sterilization system includes a medical instrument sterilization tray having a plurality of holes formed therein. A grommet apparatus is removably positioned within one of the plurality of holes, the grommet apparatus having a base structure, a top structure connected to the base structure with a plurality of sidewalls, wherein an aperture having a central axis is formed interior of the plurality of sidewalls, and at least one flexible bowed structure having a first end, a second end and a middle portion, wherein the at least one flexible bowed structure is connected to the base structure at the first end and the top structure at the second end, wherein the middle portion is positioned within the aperture. At least one medical instrument has a shaft, wherein the shaft is positioned within the aperture of the grommet apparatus, wherein the at least one flexible bowed structure frictionally biases the shaft.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
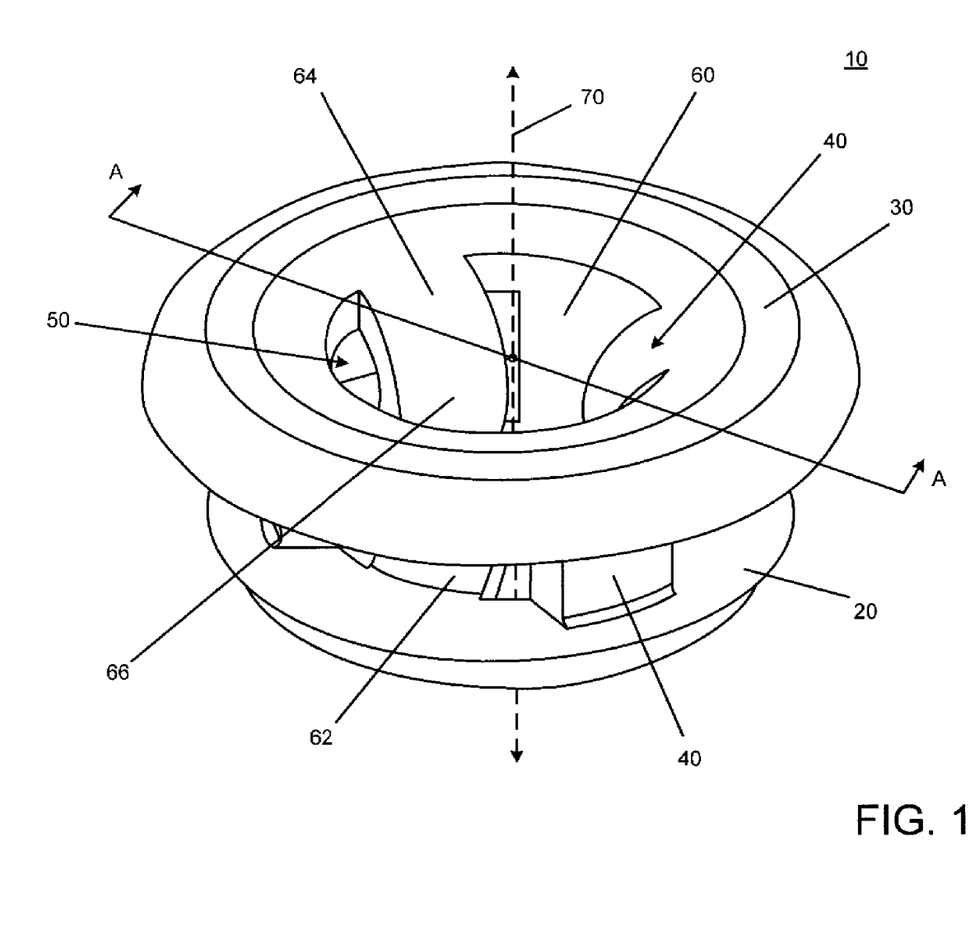
FIG. 1 is a plan view illustration of a grommet device, in accordance with a first exemplary embodiment of the present disclosure.

FIG. 1 is a plan view illustration of a grommet device 10, in accordance with a first exemplary embodiment of the present disclosure. The grommet device 10, which may be referred to as 'device 10,' includes a base structure 20 and a top structure 30. The top structure 30 is connected to the base structure 20 with a plurality of sidewalls 40. An aperture 50 having a central axis 70 is formed interior of the plurality of sidewalls 40. At least one flexible bowed structure 60 has a first end 62, a second end 64 and a middle portion 66. The flexible bowed structure 60 is connected to the base structure 20 at the first end 62 and the top structure 30 at the second end 64, wherein the middle portion 66 is positioned within the aperture 50.

The device 10 may be used with medical tool holding structures, such as sterilization trays used for holding medical instruments during a sterilization process. Accordingly, the device 10 may be used in any industry utilizing medical tools, such as tools, instruments, or any other type of implement used for surgical procedures, operations, or other medical procedures. For example, the device 10 may be used to hold medical instruments in surgical environments before, during and/or after a surgical procedure, or a medical instrument sterilization process. Similarly, the device 10 may be used with dental instruments for dental operations, routine cleanings, or for any other use. Other settings and uses within the medical field are also envisioned, all of which are considered within the scope of the present disclosure.

Figure 2:
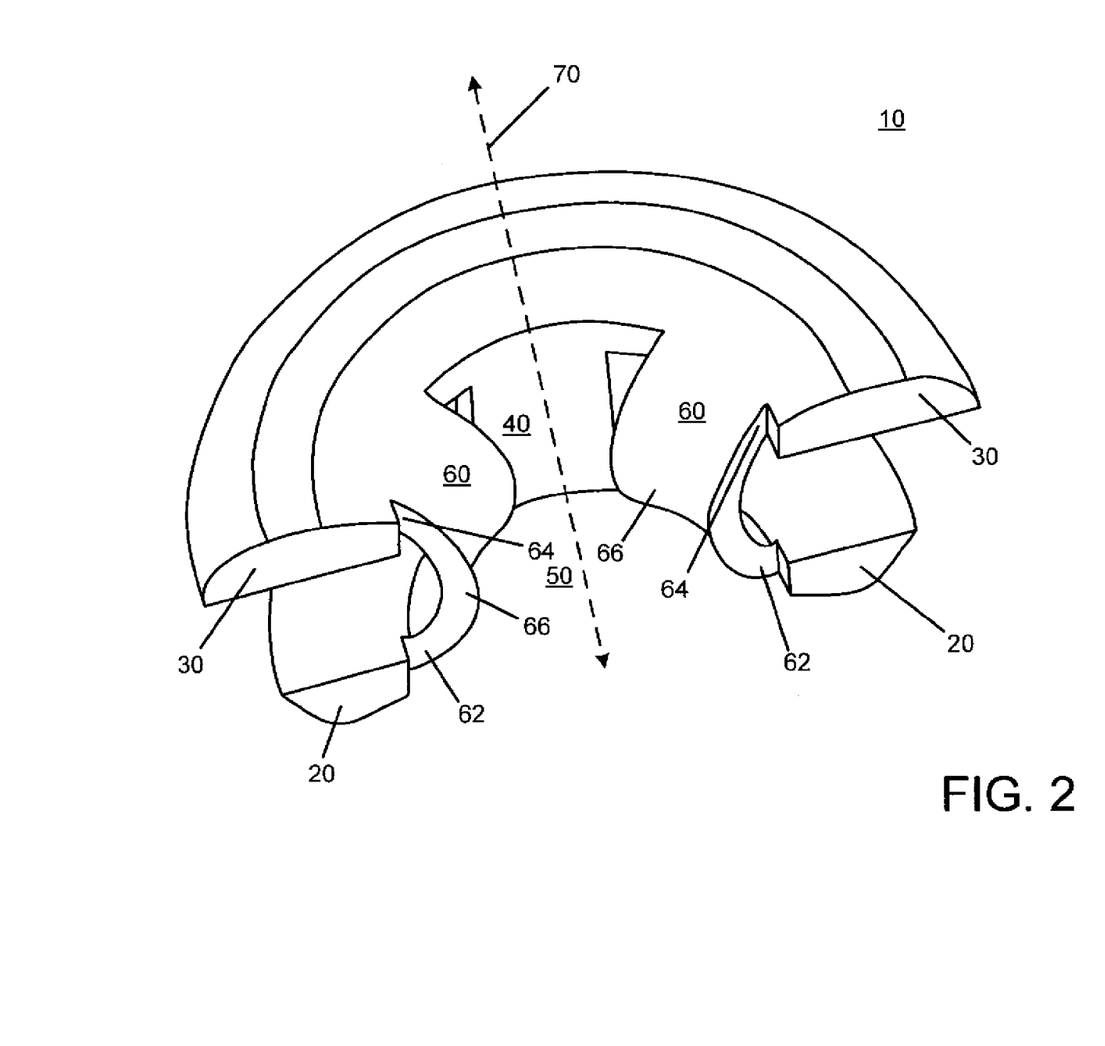
FIG. 2 is a cutout view illustration of the grommet device along the line A-A of FIG. 1, in accordance with the first exemplary embodiment of the present disclosure.

FIG. 2 is a cutout view illustration of the grommet device 10 along the line A-A of FIG. 1, in accordance with the first exemplary embodiment of the present disclosure. As is shown in FIGS. 1-2, the base structure 20 and the top structure 30 may be positioned to substantially oppose each other, with the plurality of sidewalls 40 positioned therebetween. The device 10 is designed for use with a grommet-holding structure, such as a medical instrument tray with openings, holes, or other structures, which can secure the device 10 in place. The base structure 20 may be sized larger than the grommet-holding structure, thereby allowing the base structure 20 to be retained in position abutting one side of the grommet-holding structure. For example, many sterilization trays include a plurality of holes for holding medical instruments. To secure the medical instrument properly during a medical sterilization process, the device 10 may be inserted into the hole by pushing the base structure 20 through the hole until the base structure 20 is located on one side of the tray, and the top structure 30 is located on an opposing side of the tray. In this example, the hole within the sterilization tray may be the grommet-holding structure. When the base structure 20 is positioned below the grommet-holding structure, the base structure 20 may secure the device 10 in place. In this position, the base structure 20 may be positioned interior of, or below the medical sterilization tray.

Similar to the base structure 20, the top structure 30 may be sized larger than the grommet-holding structure. This may prevent the device 10 from slipping or moving out of position within the grommet-holding structure. However, in comparison with the base structure 20, the top structure 30 may be sized larger to ensure that the device 10 does not move when a medical instrument is inserted therein. This may allow the device 10 to be inserted into the grommet-holding structure by pushing the base structure 20 through the grommet-holding structure until the plurality of sidewalls 40 are properly located within the grommet-holding structure. In this position, the larger top structure 30, in comparison to the base structure 20, may prevent the device 10 from moving further into the grommet-holding structure. Accordingly, the larger top structure 30 may be designed such that it is unable to be pushed into, or through, the grommet-holding structure.

It is noted that the base structure 20 and the top structure 30 may be sized to substantially prevent any convenient or easy removal of the device 10, since removing the device 10 may cause damage to the various components of the device 10. For example, removing the device 10 may cause separations between the various connected structures, including the base structure 20, the top structure 30, and the plurality of sidewalls 40. In addition, in some instances, removing the device 10 from the grommet-holding structure may increase or provoke contamination of a surface of the device 10 with bacteria, since bacteria harbored within portions of the device 10 may be exposed. Accordingly, the device 10 is primarily intended as a permanent structure that is not removed from the grommet-holding structure. However, various alterations and changes may be included with the device 10 which may allow the device 10 to be more easily removed, if desired.

The plurality of sidewalls 40 may include any number of sidewalls 40, such as three as is shown in FIG. 1. Commonly, the number of sidewalls 40 may depend on the size of the device 10 and the number of flexible bowed structures 60 included with the device. The plurality of sidewalls 40 may integrally connect the base structure 20 to the top structure 30. For example, the plurality of sidewalls may be oriented substantially perpendicular to the planar surfaces of the top structure 30 and the base structure 20, thereby spacing the top structure 30 and the base structure 20 a predetermined distance from one another. When the device 10 is in an in-use position with a grommet-holding structure, the plurality of sidewalls 40 may directly abut a portion of the grommet-holding structure. For example, the plurality of sidewalls 40 may be positioned abutting the grommet-holding structure, with the top structure 30 contacting an upper surface of the grommet-holding structure. The base structure 20 may be positioned opposing the top structure 30, with the grommet-holding structure therebetween. Further discussion of the placement of the device 10 is provided with regards to FIG. 5.

Additionally, the size of the sidewalls 40 may vary depending on the design. For example, the sidewalls 40 may be relatively small structures in comparison to the overall size of the device 10, as is shown in FIGS. 1-2. In one of many alternatives, the sidewalls 40 may be integrally formed together, thereby providing a substantially unitary structure that connects the base structure 20 with the top structure 30. This may include a design where the sidewalls 40 are integrally formed about an entire circumference of the aperture 50, or any portion of the circumference of the aperture 50.

The aperture 50 may be positioned within the device 10, interior of the sidewalls 40 and generally between the base structure 20 and the top structure 30. In other words, the aperture 50 generally runs through each of the base structure 20 and the top structure 30, and is positioned substantially at a center point of each. As is shown in FIGS. 1-2, this configuration positions the aperture 50 substantially interior of the sidewalls 40, which are positioned around a perimeter of the aperture 50. Of course, other designs and configurations are possible, all of which are considered within the scope of the present disclosure.

The aperture 50 may be characterized as a cavity, a cutout of material, or hole, which is positioned within the device 10, commonly aligned along a central axis 70 of the cylindrical shape of the device 10. This central axis 70 may run through a center point of the grommet-holding structure, or may be positioned off-center, as various designs may dictate. The aperture 50 may be sized to hold any type of medical instrument, and thus, may have any size diameter. The aperture 50 includes an interior space, which may be defined by an interior sidewall of the sidewalls 40. The interior space may be characterized as the space within the aperture 50 that is surrounded by any of the top structure 30, the base structure 20, and the sidewalls 40.

Any of the components of the device 10, including the base and top structures 20, 30, the sidewalls 40 and the aperture 50, may have any sizes. For example, a variety of interior and exterior diameters, thicknesses, or other dimensions may be included with the device 10. Similarly, the overall dimensions of the device 10, including the overall thickness and external diameter may have any size. For example, the device 10 may be constructed with different overall sizes to accommodate various types of medical instruments, or various grommet-holding structures. All variations are considered within the scope of the present disclosure.

The at least one flexible bowed structure 60 may include any number of flexible bowed structures 60, such as three flexible bowed structures 60, as is shown in FIG. 1. Each of the flexible bowed structures 60 that are included is connected between the top structure 30 and the base structure 20. Accordingly, a first end 62 of each of the flexible bowed structures 60 is connected to the base structure 20 and a second end 64 of each of the flexible bowed structures 60 is connected to the top structure 30. The connections may generally be integral connections, but other connections are feasible. The middle portion 66 of each of the flexible bowed structures 60, i.e., the portion of the flexible bowed structure 60 that is located between the first end 62 and the second end 64, is positioned within the aperture 50 to contact a medical instrument that is inserted therein.

The size of the flexible bowed structures 60 and the positioning of the middle portion 66 within the aperture 50 may vary depending on the design of the device 10, and the intended use of the device 10. For example, the middle portions 66 of each of the flexible bowed structures 60 may be sized to be positioned closer towards the center axis 70 if the device 10 is intended to hold small medical instruments, or positioned further away from the center axis 70 is the device 10 is intended to hold larger medical instruments. As one skilled in the art can see, many sizes and positions may be used to accommodate a variety of medical instruments, with one or a plurality of different sized devices 10. Similarly, many variations with connections between the various components may also be feasible, such as where the first end 62 and/or second end 64 of the flexible bowed structures 60 are connected to a sidewall 40. When a plurality of flexible bowed structures 60 are used, they may be located in alternating positions with the sidewalls 40. When this configuration is used, the distance between two of the sidewalls may be greater than a distance between two of the flexible bowed structures 60, thereby allowing the flexible bowed structures 60 to contact a medical instrument within the aperture 50.

The flexible bowed elements 60, which may also be referred to as prongs, tabs, or arches, may each have a shape that allows for flexibility when biased by a force; namely, the force from a medical instrument inserted into the aperture 50. For example, as is shown, the middle portion 66 of each of the flexible bowed structures 60 is arced or curved, such that it is positioned radially interior of the first end 62 and the second end 64. When a force is applied to the middle portion 66, the first and second ends 62, 64 of the flexible bowed structures 60 may be pushed away from the middle portion 66. However, since the first and second ends 62, 64 are connected securely to the base and top structures 20, 30, respectively, the relative positioning of the first and second ends 62, 64 stays substantially constant, regardless of what force is applied to the middle portion 66. Accordingly, the middle portion 66 may present a countering force on any object is inserted within the aperture 50 and contacts it. This allows for flexing or bending of the flexible bowed structures 60 when they're subjected to the force of an inserted medical instrument. As one having skill in the art can see, the flexibility of the flexible bowed structures 60 may be dependent with or relative to other components, including the properties of the material(s) that the device 10 is constructed from.

The flexible bowed structures 60 may be constructed from a flexible material, such as silicon, thereby allowing the flexible bowed structures 60 to flex and move when contacted by a medical instrument. The overall shape and size of the flexible bowed structures 60 may vary according to the design and intended use of the device 10. For example, as is shown in FIGS. 1-2, the flexible bowed structures 60 may be positioned to bow or arch inwards towards the center axis 70, thereby obstructing some of the space of the aperture 50. When a medical instrument is inserted into the aperture 50, the flexible bowed structures 60 may be biased towards the sidewalls 40. This may lessen an obstruction of the aperture 50 from the flexible bowed structures 60 and may also place the flexible bowed structures 60 in a biased state, where they continually push inwards towards the center axis 70. When the medical instrument is at least partially positioned interior of the flexible bowed structures 60, the force exerted by the flexible bowed structures 60 on the medical instrument may retain the medical instrument in a substantially stationary position.

The device 10 may be a substantially cylindrical structure around the base structure 20, the top structure 30, and the sidewalls 40, all of which may be integrally connected. The flexible bowed structures 60 may be integrally formed with the top structure 30, the sidewalls 40, and/or the base structure 20, thereby making the device 10 a substantially unitary structure. Alternatively, various parts or components of the device 10 may be formed separately and permanently or non-permanently affixed together. Commonly, the device 10 may be constructed from a rubber or silicon material that is substantially resistant to degradation from use and from sterilization environments. Within the medical industry, medical instruments are often sterilized in autoclaves, which utilize high temperatures, high pressures, moisture, and/or chemicals to sterilize a medical instrument.

Figure 3:
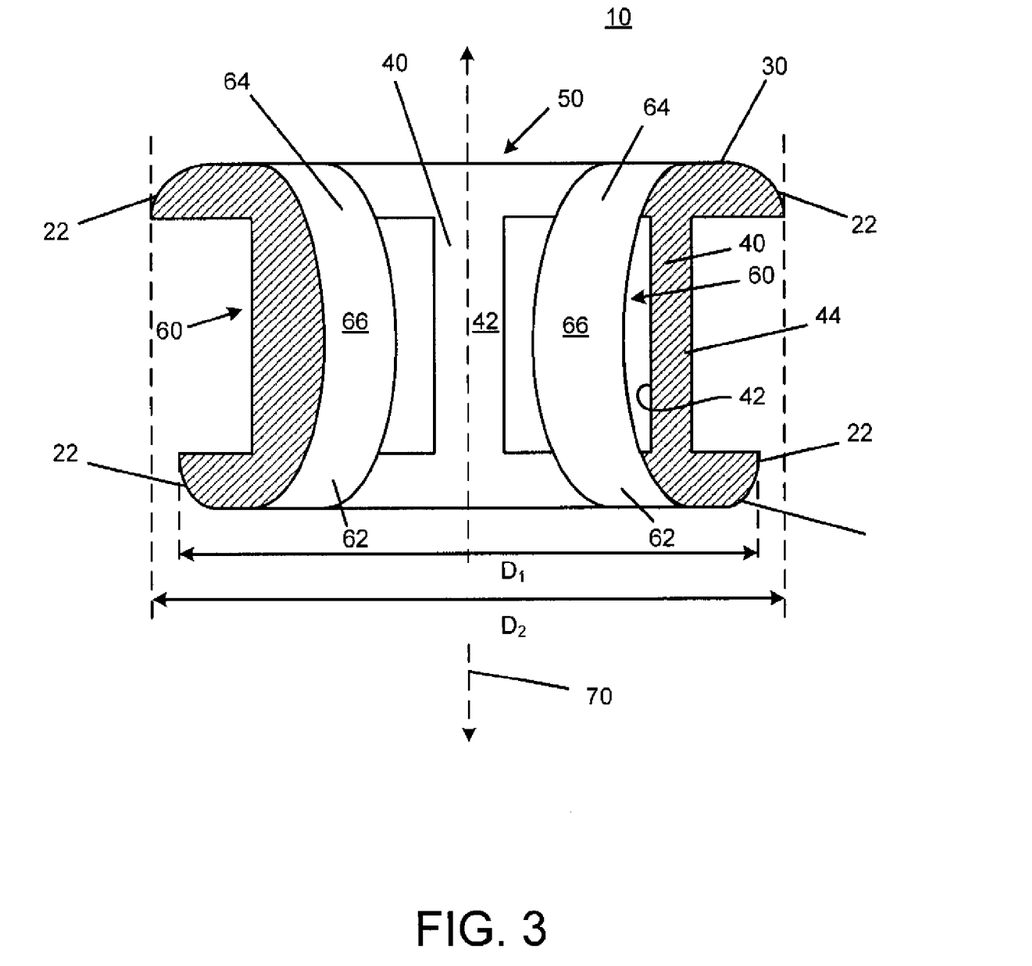
FIG. 3 is a cross-sectional view illustration of the grommet device, in accordance with the first exemplary embodiment of the present disclosure.

FIG. 3 is a cross-sectional view illustration of the grommet device 10, in accordance with the first exemplary embodiment of the present disclosure. As is shown, the diameter $D_1$ of the base portion 20 may be less than the diameter $D_2$ of the top portion 30. This sizing allows the base portion 20 to be inserted into a hole of a medical instrument sterilization tray, thereby allowing the grommet device 10 to be secured within the hole appropriately. The grommet device 10 may be sized to allow the sidewalls 40 between the top and base portions 30, 20 to substantially fit the interior diameter of a hole within the medical instrument sterilization tray.

Both the top and base portions 30, 20 of the grommet device 10 may have an outer edge 22 circumferentially positioned about the central axis 70, while the plurality of sidewalls 40 may each have an inner surface 42 and an outer surface 44, where the inner surface 42 faces and substantially defines the aperture 50 and the outer surface 44 faces oppositely from the aperture 50. The outer surface 44 of each of the plurality of sidewalls 40 may be positioned between the outer edge 22 of the top structure 30 and base structure 20, and the central axis 70. In other words, the outer edge 22 of the top and base structures 30, 20 may extend further away from the aperture 50 than the outer surface 44 of the sidewall 40. This sizing of the grommet device 10 may allow for the medical instrument sterilization tray to securely fit proximate to the outer surface 44 of the sidewall 40 and between the top and bottom portions 30, 20.

Figure 4:
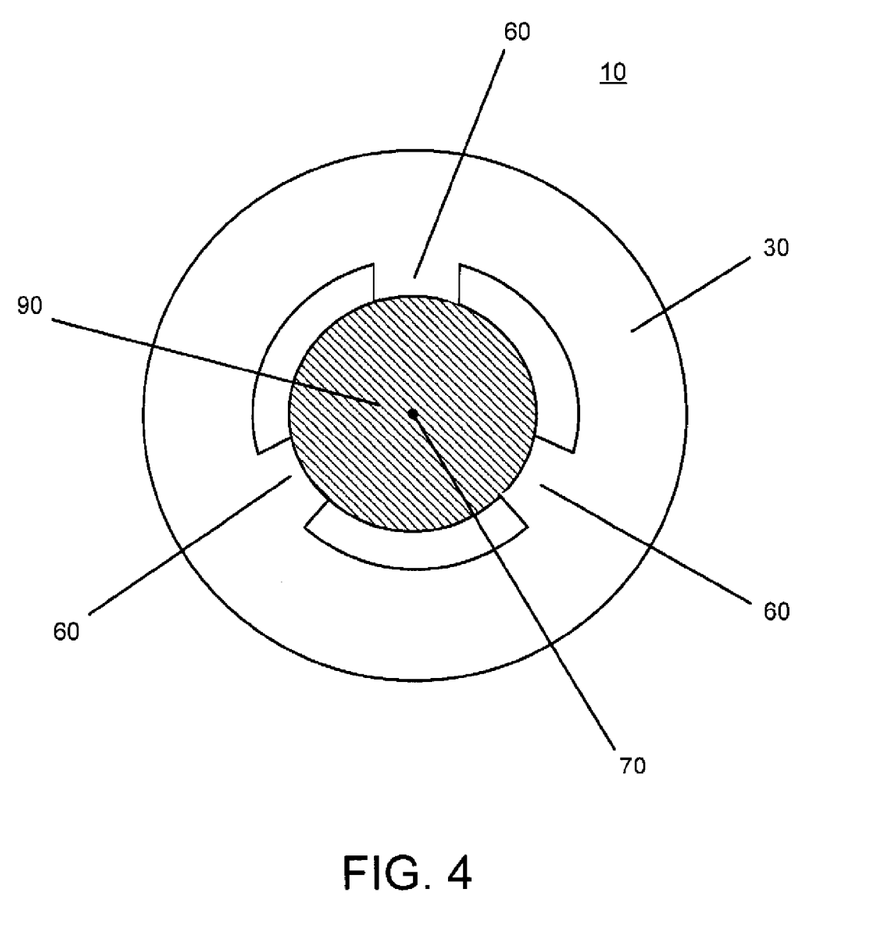
FIG. 4 is a top view illustration of the grommet device, in accordance with the first exemplary embodiment of the present disclosure.

FIG. 4 is a top view illustration of the grommet device 10, in accordance with the first exemplary embodiment of the present disclosure. As is shown, the flexible bowed structures 60 may each be integral with the top structure 30 and the base structure 20, and bow inwards towards the center axis 70 (illustrated as a point perpendicular to the plane of the paper). Any number of flexible bowed structures 60 may be included with the device 10. As previously mentioned, FIGS. 1-5 generally illustrate three flexible bowed structures 60 with the device 10, but any number may be used. This may include only one flexible bowed structure 60, or a plurality of flexible bowed structures 60 such as five or more. The overall area of the aperture 50 may be determined relative to the number of flexible bowed structures 60 within the device 10 and their respective positions. For example, the greater the shaft diameter of a medical instrument, the more the flexible bowed structures 60 may flex away from the center axis 70, the larger the overall aperture 50 size may be. All variations, configurations and possible designs are considered within the scope of the present disclosure.

Figure 5:
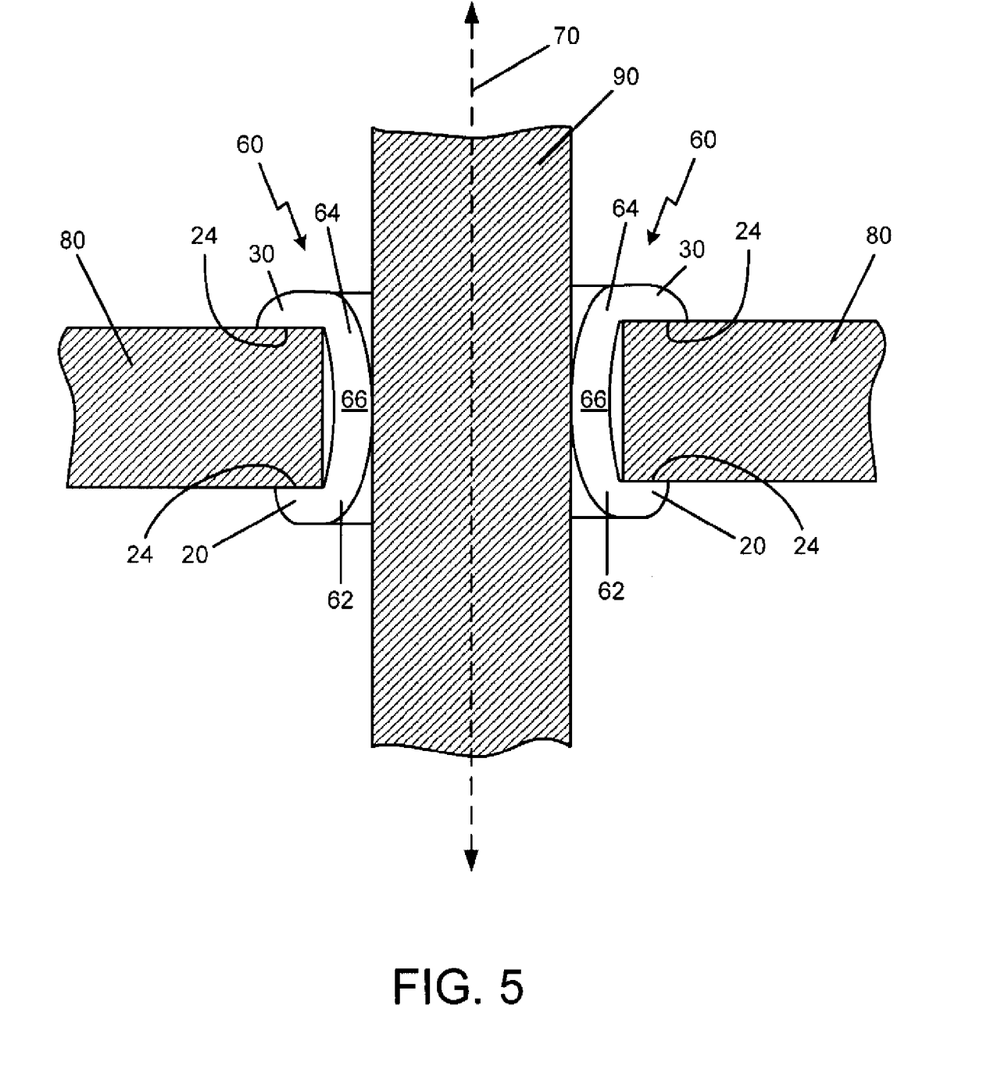
FIG. 5 is a cross-sectional view illustration of the grommet device positioned in use with a grommet-holding structure and medical instrument, in accordance with the first exemplary embodiment of the present disclosure.

FIG. 5 is a cross-sectional view illustration of the grommet device 10 positioned in use with a grommet-holding structure and medical instrument 90, in accordance with the first exemplary embodiment of the present disclosure. The grommet-holding structure 80, which may be any type of sterilization tray, or other structure capable of holding the device 10, is shown with the base structure 20 of the device 10 positioned on one side and the top structure 30 positioned on an opposing side. Thus, the device 10 is at least partially positioned within the opening, hole, or aperture within a grommet-holding structure 80 and a medical instrument 90 is shown in the in-use position with the device 10.

As is shown, the medical instrument 90 may be one with a shaft or similar structure that allows for insertion into the aperture 50. For example, the medical instrument 90 may be a scalpel, or other tool, wherein the shaft of the medical instrument 90 biases the middle portions 66 of each of the flexible bowed structures 60 away from the center axis 70. Since the flexible bowed structures 60 are designed to move towards their original position when biased, i.e., a position where the flexible bowed structures 60 are each bowing towards the center axis 70, the flexible bowed structures 60 may create an inward force on the medical instrument 90. In other words, the natural flex of the flexible bowed structures 60 may subject a force on the medical instrument 90 towards the center axis 70. This force, or combination of forces when a plurality of flexible bowed structures 60 is used, may successfully retain the medical instrument 90 in a proper position. In this position, the medical instrument 90, device 10, and grommet-holding structure 80 may be easily transported or subjected to a sterilization process without the dislodging of the medical instrument 90 from the device 10, and the device 10 from the grommet-holding structure 80.

As can be seen in FIG. 5, the base and top portions 20, 30 of the grommet device 10 may create a seal with the grommet-holding structure 80. The seal may be created with a sealing edge 24 within either or both of the top structure 30 and the base structure 20. In FIG. 5, both the top and base structures 30, 20 are shown with a sealing edge 24. The sealing edge 24 creates a seal between both the top structure 30 and the base structure 20 and the grommet-holding structure 80 when the grommet device 10 is positioned within the hole of the grommet-holding structure 80. Commonly, the top and base structures 30, 20 will have a substantially planar edge for interfacing with the medical instrument tray, thereby making the sealing edge substantially planar in shape. The seal may prevent bacteria and other harmful substances from gaining access to any space between the grommet device 10 and the medical instrument sterilization tray, which will provide a safe and effective sterilization environment for the medical instruments 90.

Figure 6:
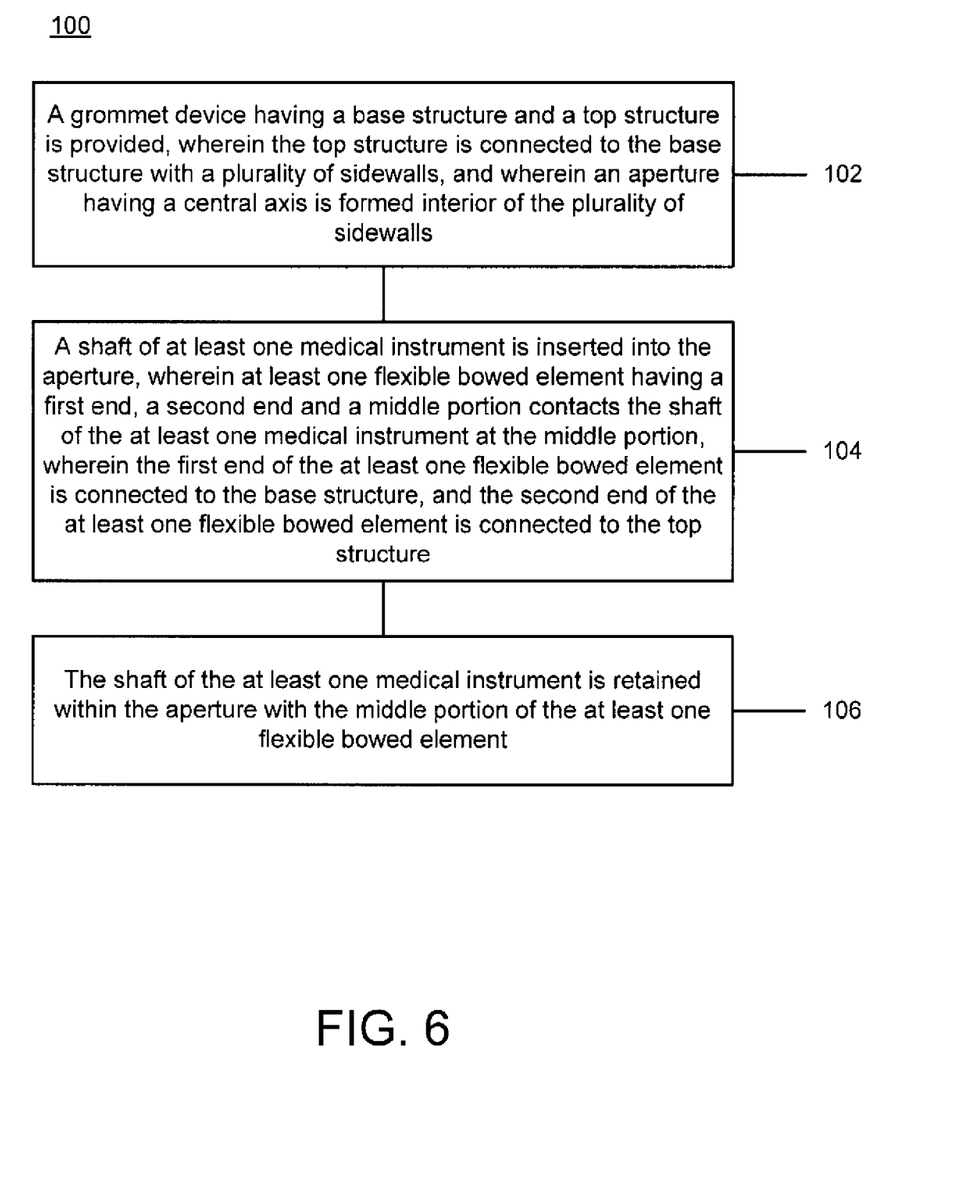
FIG. 6 is a flowchart illustrating a method of constructing a grommet device, in accordance with the first exemplary embodiment of the disclosure.

FIG. 6 is a flowchart 100 illustrating a method securing a medical instrument within sterilization tray, in accordance with a second exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a grommet device having a base structure and a top structure is provided, wherein the top structure is connected to the base structure with a plurality of sidewalls, and wherein an aperture having a central axis is formed interior of the plurality of sidewalls. A shaft of at least one medical instrument is inserted into the aperture, wherein at least one flexible bowed element having a first end, a second end and a middle portion contacts the shaft of the at least one medical instrument at the middle portion, wherein the first end of the at least one flexible bowed element is connected to the base structure, and the second end of the at least one flexible bowed element is connected to the top structure (block 104). The shaft of the at least one medical instrument is retained within the aperture with the middle portion of the at least one flexible bowed element (block 106).

Many additional steps and variations may be included with the method, including any of the functions, steps, or processes described within this disclosure. For example, inserting the shaft of the at least one medical instrument into the aperture may include biasing the middle portion of the at least one flexible bowed element radially outwards from the central axis. Once the medical instrument is positioned within the grommet device, it may be subjected to a sterilization process, wherein the medical instrument is retained within the at least one grommet device throughout the sterilization process, and wherein the medical instrument is only contacted by the grommet device.

It may be common for the grommet device to be removed and replaced. This procedure may first include identifying at least one state of the grommet device, wherein the state includes the grommet device having a damaged state, an unsanitary state, or an unclean state. The grommet device may then be removed from the hole of the sterilization tray and a new grommet device may be positioned within the hole of the sterilization tray. When inserting and retaining a grommet device into the hole, a user may force the base portion of the grommet device through the hole without moving the top portion of the grommet device through the hole. Once in place, the grommet device may create a seal between a sealing edge within at least one of the top structure and the base structure, and the sterilization tray. The seal may prevent bacterial substances from moving between the grommet device and the sterilization tray with the seal.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claim.

What is claimed is:

1. A grommet device comprising:
   a base structure;
   a top structure, the top structure connected to the base structure with a plurality of sidewalls, wherein an aperture having a central axis is formed interior of the plurality of sidewalls; and
   at least one flexible bowed structure having a first end, a second end and a middle portion, the at least one flexible bowed structure connected to the base structure at the first end and the top structure at the second end, wherein the middle portion is positioned within the aperture.

2. The grommet device of claim 1, wherein the base structure has a first diameter and the top structure has a second diameter, wherein second diameter is greater than the first diameter.

3. The grommet device of claim 1, further comprising a sealing edge within at least one of the top structure and the base structure, wherein the sealing edge creates a seal between the at least one top structure and the base structure, respectively, and a medical sterilization tray, when the sealing edge is positioned proximate to the medical instrument sterilization tray.

4. The grommet device of claim 3, wherein the sealing edge is substantially planar.

5. The grommet device of claim 1, wherein the plurality of sidewalls is positioned substantially perpendicular to the base structure and top structure.

6. The grommet device of claim 1, wherein each of the top structure and base structure further comprise an outer edge positioned circumferentially about the central axis.

7. The grommet device of claim 6, wherein the plurality of sidewalls each have an inner surface and an outer surface, wherein the inner surface faces the aperture and the outer surface faces oppositely from the aperture, wherein the outer surface of each of the plurality of sidewalls is positioned between the outer edge of the top structure and base structure, and the central axis.

8. The grommet device of claim 1, wherein the at least one flexible bowed structure further comprises at least three flexible bowed structure.

9. The grommet device of claim 8, wherein plurality of sidewalls and the at least three flexible bowed structures are located in alternating positions.

10. The grommet device of claim 9, wherein a distance between two of the plurality of sidewalls is greater than a distance between two of the at least three flexible bowed structures.

11. The grommet device of claim 1, wherein the middle portion of the at least one flexible bowed structure is positioned radially interior of the first end and second end.

12. A medical instrument sterilization system comprising:
    a medical instrument sterilization tray having a plurality of holes formed therein;
    a grommet apparatus removably positioned within one of the plurality of holes, the grommet apparatus having a base structure, a top structure connected to the base structure with a plurality of sidewalls, wherein an aperture having a central axis is formed interior of the plurality of sidewalls, and at least one flexible bowed structure having a first end, a second end and a middle portion, wherein the at least one flexible bowed structure is connected to the base structure at the first end and the top structure at the second end, wherein the middle portion is positioned within the aperture; and
    at least one medical instrument having a shaft, wherein the shaft is positioned within the aperture of the grommet apparatus, wherein the at least one flexible bowed structure frictionally biases the shaft.

13. The medical instrument sterilization system of claim 12, wherein the at least one flexible bowed structure contacts the shaft at the middle portion of the at least one flexible bowed structure.

14. A method of securing a medical instrument within sterilization tray, the method comprising the steps of:
    providing a grommet device having a base structure and a top structure, wherein the top structure is connected to the base structure with a plurality of sidewalls, and wherein an aperture having a central axis is formed interior of the plurality of sidewalls;
    inserting a shaft of at least one medical instrument into the aperture, wherein at least one flexible bowed element having a first end, a second end and a middle portion contacts the shaft of the at least one medical instrument at the middle portion, wherein the first end of the at least one flexible bowed element is connected to the base structure, and the second end of the at least one flexible bowed element is connected to the top structure; and
    retaining the shaft of the at least one medical instrument within the aperture with the middle portion of the at least one flexible bowed element.

15. The method of claim 14, wherein inserting the shaft of the at least one medical instrument into the aperture further comprises biasing the middle portion of the at least one flexible bowed element radially outwards from the central axis.

16. The method of claim 14, further comprising the step of subjecting the medical instrument to a sterilization process, wherein the medical instrument is retained within the at least one grommet device throughout the sterilization process, and wherein the medical instrument is only contacted by the grommet device.

17. The method of claim 14, further comprising the step of retaining the grommet device into a hole of the sterilization tray by forcing the base portion of the grommet device through the hole without moving the top portion of the grommet device through the hole.

18. The method of claim 14, further comprising the steps of:
    identifying at least one state of the grommet device, wherein the at least one state includes the grommet device having a damaged state, an unsanitary state, and an unclean state;
    removing the grommet device from a hole of the sterilization tray; and positioning a new grommet device within the hole of the sterilization tray.

19. The method of claim 14, further comprising the step of creating a seal between a sealing edge within at least one of the top structure and the base structure, and the sterilization tray.

20. The method of claim 19, further comprising the step of preventing a bacterial substance from moving between the grommet device and the sterilization tray with the seal.

* * * * *